United States Patent [19]

Cottman

[11] Patent Number: 5,672,730
[45] Date of Patent: Sep. 30, 1997

[54] THIOPROPIONATE SYNERGISTS

[75] Inventor: Kirkwood Storer Cottman, Akron, Ohio

[73] Assignee: The Goodyear Tire & Rubber Company, Akron, Ohio

[21] Appl. No.: 532,972

[22] Filed: Sep. 22, 1995

[51] Int. Cl.$^6$ .................................................. C07C 321/00
[52] U.S. Cl. ........................... 560/152; 560/54; 252/406; 252/401; 252/402; 524/285; 524/289; 524/304; 524/303
[58] Field of Search ............................ 560/154, 152; 252/406, 401, 402; 524/285, 289, 304, 303

[56] References Cited

U.S. PATENT DOCUMENTS

| | | | |
|---|---|---|---|
| 3,758,549 | 9/1973 | Dexter et al. | 260/481 |
| 4,216,116 | 8/1980 | Kline | 252/404 |
| 4,254,020 | 3/1981 | Kline | 260/45.85 |
| 4,301,296 | 11/1981 | Kuczkowski | 560/152 |
| 4,774,355 | 9/1988 | Omori et al. | 560/152 |
| 5,093,517 | 3/1992 | Cottman et al. | 560/152 |

*Primary Examiner*—Samuel Barts
*Attorney, Agent, or Firm*—Bruce J. Hendricks

[57] ABSTRACT

The present invention relates to a compound of the formula

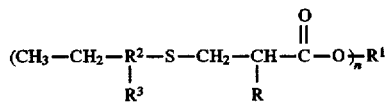

wherein n is an integer from 1 to 4, R is selected from the group consisting of hydrogen and methyl; wherein when n is 1, $R^1$ is selected from the group consisting of alkyl radicals having 1 to 18 carbon atoms, aryl radicals having 6 to 12 carbon atoms, aralkyl radicals having 7 to 12 carbon atoms, cycloalkyl radicals having 5 to 12 carbon atoms and radicals of the formula:

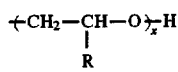

wherein x is an integer of from 1 to 7; wherein when n is 2, $R^1$ is selected from the group consisting of alkylene radicals having 2 to 18 carbon atoms, cycloalkylene radicals having 5 to 12 carbon atoms, arylene radicals having 6 to 12 carbon atoms,

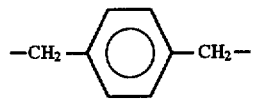

polyalkyl glycol ether radicals having the following structure

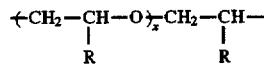

wherein x is an integer from 1 to 7.

12 Claims, No Drawings

5,672,730

THIOPROPIONATE SYNERGISTS

BACKGROUND OF THE INVENTION

Those skilled in the art of the polymer stabilization are constantly searching for new and more effective antioxidant systems. The need for such improved systems is the result of using polymers under more and more demanding and rigorous conditions. In particular, the use of polymers in automotive applications and the like, for example as gaskets, has subjected polymers to high temperatures for great periods of time, thereby requiring long lasting and persistent protection.

U.S. Pat. No. 4,301,296 discloses the stabilization of SBR and NBR polymers with at least one amine antioxidant and at least one ester of the formula.

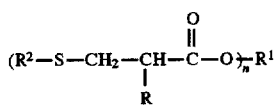

wherein n is an integer from 1 to 4, wherein R is selected from the group consisting of hydrogen and methyl, wherein when n is 1, $R^1$ is selected from the group consisting of alkyl radicals having 1 to 18 carbon atoms, aryl radicals having 6 to 12 carbon atoms, aralkyl radicals having 7 to 12 carbon atoms and cycloalkyl radicals having 5 to 12 carbon atoms wherein when n is 2, $R^1$ is selected from the group consisting of alkylene radicals having 2 to 18 carbon atoms, cycloalkylene radicals having 5 to 12 carbon atoms, arylene radicals having 6 to 12 carbon atoms,

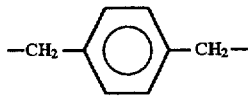

polyalkyl glycol ether radicals having the following structure

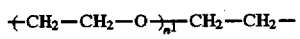

wherein $n^1$ is an integer from 1 to 7, a thioether radical having the following structure

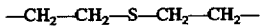

wherein when n is 3 or 4, $R^1$ is an aliphatic hydrocarbon radical having the formula $C_yH_{2y+2-n}$, wherein y is an integer from 3 to 6 and wherein $R^2$ is selected from the group consisting of alkyl radicals having 1 to 24 carbon atoms, aryl radicals having 6 to 12 carbon atoms and aralkyl radicals having 7 to 12 carbon atoms.

A commercially available ester of the above formula is 3,6,9-trioxaundecane-1,11-bis(3-n-dodecylthiopropionate) which is sold under the designation Wingstay® SN-1 from The Goodyear Tire & Rubber Company. This ester has a waxy texture and is solid below 28° C. When used, the ester is generally heated above 40° C. before it can be removed from its container before it can be added to the polymer for mixing.

SUMMARY OF THE INVENTION

The present invention relates to new and useful compounds for use as synergists. Through discovery of this invention, the thiopropionate synergists may be used to more easily solubize high melting rubber chemicals and to make emulsions with higher solids with greater stabilities and lower viscosities.

DETAILED DESCRIPTION OF THE INVENTION

There is disclosed a compound of the formula

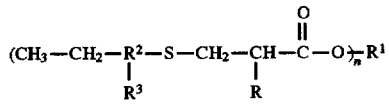

wherein n is an integer from 1 to 4, R is selected from the group consisting of hydrogen and methyl; wherein when n is 1 R1 is selected from the group consisting of alkyl radicals having 1 to 18 carbon atoms, aryl radicals having 6 to 12 carbon atoms, aralkyl radicals having 7 to 12 carbon atoms, and radicals of the formula:

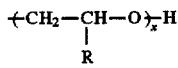

wherein x is an integer of from 1 to 7; cycloalkyl radicals having 5 to 12 carbon atoms; wherein when n is 2, $R^1$ is selected from the group consisting of alkylene radicals having 2 to 18 carbon atoms, cycloalkylene radicals having 5 to 12 carbon atoms, arylene radicals having 6 to 12 carbon atoms,

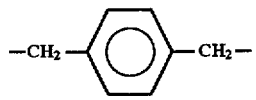

polyalkyl glycol ether radicals having the following structure

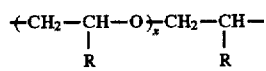

wherein x is an integer from 1 to 7, a thioether radical having the following structure

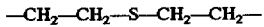

and wherein when n is 3 or 4, $R^1$ is an aliphatic hydrocarbon radical having the formula $C_yH_{2y+2-n}$ and wherein y is an integer from 3 to 6; $R^2$ is an alkylene radical ranging from 6 to 9 carbon atoms; $R^3$ is an alkyl radical ranging from 1 to 4 carbon atoms; with the proviso that the total sum of the number of carbon atoms for $R^2$ and $R^3$ equal 10.

The esters of the present invention are illustrated by the following compounds: 3,6,9 -trioxaundecane-1,11-bis[3-(2-butyloctyl)thiopropionate]; 3,6-dioxaoctane-1,8-bis[3-(2-butyloctyl)thiopropionate]; 3,6,9-trioxaundecane-1,11-bis [3-(2-butyloctyl)thio-2-methylpropionate]; 3-oxapentane-1, 5-bis[3-(2-butyloctyl)thiopropionate]; phenyl-[3-(2-butyloctyl)thiopropionate]; phenyl-1,4-bis[3-(2-butyloctyl) thiopropionate]; naphthyl-1-[3-(2-butyloctyl) thiopropionate]; naphthyl-2-[3-(2-butyloctyl)2-methyl thiopropionate]; naphthyl-1,4-bis[3-(2-butyloctyl) thiopropionate]; phenyl-[3-(2-butyloctyl)thio-2-methylpropionate]; benzyl-[3-(2-butyloctyl) thiopropionate]; benzyl-[3-(2-butyloctyl)thio-2- methylpropionate]; p-xylyl-alpha, alpha'-bis[3-(2-butyloctyl)-2-methylpropionate]; o-xylyl-alpha, alpha'-bis[3-(2-butyloctyl)thiopropionate]; ethane-1,2-bis[3-(2-butyloctyl)thiopropionate]; butane-1,4-bis[3-(2-butyloctyl)thiopropionate]; pentane-1,5-bis[3-(2-butyloctyl)thio-2-methylpropionate]; propane-1,2-bis[3-(2-butyloctyl)thiopropionate]; octane-1,8-bis[3-(2-butyloctyl)thiopropionate]; 3,6,9-trioxaundecane-1,11-bis[3-(2-butyloctyl)thiopropionate]; 3,6,9-trioxaundecane-1,11-bis[3-(2-butyloctyl)thio -2-methyl-propionate]; 3-oxapentane-1,5-bis[3-(2 -butyloctyl)thio-2-methylpropionate]; 3-thiapentane -1,5-bis[(2-butyloctyl)thio-2-methylpropionate]; 1,1,1-trimethanolpropane-tris[3-(2-butyloctyl)thiopropionate]; 1,1,1-trimethanolpropane -bis[3-(2-butyloctyl)thiopropionate]; pentaerythritol-tetrakis[3-(2-butyloctyl)thiopropionate]; pentaerythritol-tetrakis[3-(2-butyloctyl)thio-2-methyl-propionate]; 3,6,9-trioxaundecane-1,11-bis[3-(3-butyloctyl)thiopropionate]; 3,6-dioxaoctane-1,8-bis[3-(3-butyloctyl)thiopropionate];3, 6,9-trioxaundecane-1,11-bis[3-(3-butyloctyl)thio-2-methylpropionate]; 3-oxapentane-1,5-bis[3-(3-butyloctyl)thiopropionate]; phenyl-[3-(3-butyloctyl)thiopropionate]; phenyl-1,4-bis[3-(3-butyloctyl)thiopropionate]; naphthyl-1-[3-(3-butyloctyl)thiopropionate]; naphthyl-2-[3-(3-butyloctyl)2-methyl thiopropionate]; naphthyl-1,4-bis[3-(3-butyloctyl)thiopropionate]; phenyl-[3-(3-butyloctyl)thio-2-methylpropionate]; benzyl-[3-(2-butyloctyl)thiopropionate]; benzyl-[3-(3-butyloctyl)thio-2-methylpropionate]; p-xylyl-alpha, alpha'-bis[3-(3-butyloctyl)2-methylpropionate]; o-xylyl-alpha, alpha'-bis[3-(3-butyloctyl)thiopropionate]; ethane-1,2-bis[3-(3-butyloctyl)thiopropionate]; butane-1,4-bis[3-(3-butyloctyl)thiopropionate]; pentane-1,5-bis[3-(3-butyloctyl)thio-2-methylpropionate]; propane-1,2-bis[3-(3-butyloctyl)thiopropionate]; octane-1,8-bis[3-(3-butyloctyl)thiopropionate]; 3,6,9-trioxaundecane-1,11-bis[3-(3-butyloctyl)thiopropionate]; 3,6,9-trioxaundecane-1,11-bis [3-(3-butyloctyl)thio-2-methyl -propionate]; 3-oxapentane-1,5-bis[3-(3-butyloctyl)thio-2-methylpropionate]; 3-thiapentane -1,5-bis[(3-butyloctyl)thio-2-methylpropionate]; 1,1,1-trimethanolpropane-tris[3-(3-butyloctyl)thiopropionate]; 1,1,1-trimethanolpropane-bis[3-(3-butyloctyl)thiopropionate]; pentaerythritol -tetrakis[3-(3-butyloctyl)thiopropionate]; pentaerythritol-tetrakis[3-(3-butyloctyl)thio-2-methyl-propionate]; 3,6,9-trioxaundecane-1,11-bis[3-(4-butyloctyl)thiopropionate]; 3,6-dioxaoctane-1,8-bis[3-(4-butyloctyl)thiopropionate]; 3,6,9-trioxaundecane-1,11-bis [3-(4-butyloctyl)thio-2-methylpropionate]; 3-oxapentane-1,5-bis[3-(4-butyloctyl)thiopropionate]; phenyl-[3-(4-butyloctyl)thiopropionate]; phenyl-1,4-bis[3-(4-butyloctyl)thiopropionate]; naphthyl-1-[3-(4-butyloctyl)thiopropionate]; naphthyl-2-[3-(4-butyloctyl)2-methyl thiopropionate]; naphthyl-1,4-bis[3-(4-butyloctyl)thiopropionate]; phenyl-[3-butyloctyl)thio-2-methylpropionate], benzyl-[3-butyloctyl)thiopropionate]; benzyl-[3-(4-butyloctyl)thio-2-methylpropionate]; p-xylyl-alpha, alpha'-bis[3-(4-butyloctyl)2-methylpropionate]; o-xylyl-alpha, alpha'-bis[3-butyloctyl)thiopropionate]; ethane-1,2-bis[3-(4-butyloctyl)thiopropionate]; butane-1,4-bis[3-(4-butyloctyl)thiopropionate]; pentane-1,5-bis[3-(4-butyloctyl)thio-2-methylpropionate]; propane-1,2-bis[3-(4-butyloctyl)thiopropionate]; octane-1,8-bis[3-(4-butyloctyl)thiopropionate]; 3,6,9-trioxaundecane-1,11-bis[3-(4-butyloctyl)thiopropionate]; 3,6,9-trioxaundecane-1,11-bis [3-(4-butyloctyl)thio-2-methyl-propionate]; 3-oxapentane-1,5-bis[3-(4-butyloctyl)thio-2-methylpropionate]; 3-thiapentane-1,5-bis[(4-butyloctyl)thio-2-methylpropionate]; 1,1,1-trimethanolpropane-tris[3-(4-butyloctyl)thiopropionate]; 1,1,1-trimethanolpropane-bis[3-(4-butyloctyl)thiopropionate]; pentaerythritol-tetrakis[3-(4-butyloctyl)thiopropionate]; pentaerythritol-tetrakis[3-(4-butyloctyl)thio-2-methyl-propionate]; 3,6,9-trioxaundecane-1,11-bis[3 -(5-butyloctyl)thiopropionate]; 3,6-dioxaoctane-1,8-bis[3-(5-butyloctyl)thiopropionate]; 3,6,9-trioxaundecane-1,11-bis[3-(5-butyloctyl)thio-2-methylpropionate]; 3-oxapentane-1,5-bis[3-(5-5butyloctyl) thiopropionate]; phenyl-[3-(5-butyloctyl)thiopropionate]; phenyl-1,4-bis[3-(5-butyloctyl)thiopropionate]; naphthyl-1-[3-(5-butyloctyl)thiopropionate]; naphthyl-2-[3-(5-butyloctyl)2-methyl thiopropionate]; naphthyl-1,4-bis[3-(5-butyloctyl)thiopropionate]; phenyl-[3-(5-butyloctyl)thio-2-methylpropionate]; benzyl-[3-(5-butyloctyl) thiopropionate]; benzyl-[3-(5-butyloctyl)thio-2-methylpropionate]; p-xylyl-alpha, alpha'-bis[3-(5-butyloctyl)2-methylpropionate]; o-xylyl-alpha, alpha'-bis[3-(5-butyloctyl)thiopropionate]; ethane-1,2-bis[3-(5-butyloctyl)thiopropionate]; butane-1,4-bis[3-(5-butyloctyl) thiopropionate]; pentane-1,5-bis[3-(5-butyloctyl)thio-2-methylpropionate]; propane-1,2-bis[3-(5-butyloctyl) thiopropionate]; octane-1,8-bis[5-(5-butyloctyl)thiopropionate]; 3,6,9-trioxaundecane -1,11-bis[3-(5-butyloctyl)thiopropionate]; 3,6,9-trioxaundecane-1,11-bis [3-(5-butyloctyl)thio-2-methyl-propionate]; 3-oxapentane-1,5-bis[3-(5-butyloctyl)thio-2-methylpropionate]; 3-thiapentane -1,5-bis[(5-butyloctyl)thio-2-methylpropionate]; 1,1,1-trimethanolpropane-tris[3-(5-butyloctyl)thiopropionate]; 1,1,1-trimethanolpropane-bis[3-(5-butyloctyl)thiopropionate]; pentaerythritol-tetrakis[3-(5-butyloctyl)thiopropionate]; pentaerythritol-tetrakis[3-(5-butyloctyl)thio-2-methyl-propionate]; 3,6,9-trioxaundecane-1,11-bis[3-(2-dodecyl)thiopropionate]; 3,6-dioxaoctane-1,8-bis[3-(2-dodecyl)thiopropionate]; 3,6,9-trioxaundecane-1,11-bis[3-(2-dodecyl)thio-2-methylpropionate]; 3-oxapentane-1,5-bis[3-(2-dodecyl) thiopropionate]; phenyl-[3-(2-dodecyl)thiopropionate]; phenyl-1,4-bis[3-(2-dodecyl)thiopropionate]; naphthyl-1-[3-(2-dodecyl)thiopropionate]; naphthyl-2-[3-(2-dodecyl)2-methyl thiopropionate]; naphthyl-1,4-bis[3-(2-dodecyl) thiopropionate]; phenyl-[3-(2-dodecyl)thio-2-methylpropionate]; benzyl-[3-(2-dodecyl)thiopropionate]; benzyl-[3-(2-dodecyl)thio-2-methylpropionate]; p-xylyl-alpha, alpha'-bis[3-(2-dodecyl)2-methylpropionate]; o-xylyl-alpha, alpha'-bis[3-(2-dodecyl)thiopropionate]; ethane-1,2-bis[3-(2-dodecyl)thiopropionate]; butane-1,4-bis [3-(2-dodecyl)thiopropionate]; pentane-1,5-bis[3-(2-dodecyl)thio-2-methylpropionate]; propane-1,2-bis[3-(2-dodecyl)thiopropionate]; octane-1,8-bis[3-(2-dodecyl) thiopropionate]; 3,6,9-trioxaundecane-1,11-bis[3-(2-dodecyl)thiopropionate]; 3,6,9-trioxaundecane-1,11-bis[3-(2-dodecyl)thio-2-methyl-propionate]; 3-oxapentane-1,5-bis[3-(2-dodecyl)thio-2-methylpropionate]; 3-thiapentane-1,5-bis[(2-dodecyl)thio-2-methylpropionate]; 1,1,1-trimethanolpropane-tris[3-(2-dodecyl)thiopropionate]; 1,1,1-trimethanolpropane-bis[3-(2-dodecyl)thiopropionate]; pentaerythritol-tetrakis[3-(2-dodecyl)thiopropionate]; pentaerythritol-tetrakis[3-(2-dodecyl)thio-2-methyl-propionate]; 3,6,9-trioxaundecane-1,11-bis[3-(2-ethyldecyl) thiopropionate]; 3,6-dioxaoctane-1,8-bis[3-(2-ethyldecyl) thiopropionate]; 3,6,9-trioxaundecane-1,11-bis[3-(2-ethyldecyl)thio-2-methylpropionate]; 3-oxapentane-1,5-bis [3-(2-ethyldecyl)thiopropionate]; phenyl-[3-(2-ethyldecyl) thiopropionate]; phenyl-1,4-bis[3-(2-ethyldecyl) thiopropionate]; naphthyl-1-[3-(2-ethyldecyl) thiopropionate]; naphthyl-2-[3-(2-ethyldecyl)2-methyl thiopropionate]; naphthyl-1,4-bis[3-(2-ethyldecyl) thiopropionate]; phenyl-[3-(2-ethyldecyl)thio-2-methylpropionate]; benzyl-[3-(2 -ethyldecyl) thiopropionate]; benzyl-[3-(2-ethyldecyl)thio-2-methylpropionate]; p-xylyl-alpha, alpha'-bis[3-(2-ethyldecyl)2-methylpropionate]; o-xylyl-alpha, alpha'-bis [3-(2-ethyldecyl)thiopropionate]; ethane-1,2-bis[3-(2-ethyldecyl)thiopropionate]; butane-1,4-bis[3-(2-ethyldecyl) thiopropionate]; pentane-1,5-bis[3-(2-ethyldecyl)thio-2-methylpropionate]; propane-1,2-bis[3-(2-ethyldecyl) thiopropionate]; octane-1,8-bis[3-(2-ethyldecyl) thiopropionate]; 3,6,9-trioxaundecane-1,11-bis[3-(2-ethyldecyl)thiopropionate]; 3,6,9-trioxaundecane-1,11-bis [3-(2-ethyldecyl)thio-2-methyl-propionate]; 3-oxapentane-1,5-bis[3-(2-ethyldecyl)thio-2-methylpropionate]; 3-thiapentane-1,5-bis[(2-ethyldecyl)thio-2-methylpropionate]; 1,1,1-trimethanolpropane-tris[3-(2-ethyldecyl)thiopropionate]; 1,1,1-trimethanolpropane-bis[3-(2-ethyldecyl)thiopropionate]; pentaerythritol-tetrakis[3-(2-ethyldecyl)thiopropionate]; pentaerythritol-tetrakis[3-(2-ethyldecyl)thio-2-methyl-propionate]; 3,6,9-trioxaundecane-1,11-bis[3-(6-butyloctyl)thiopropionate]; 3,6-dioxaoctane-1,8-bis[3-(6-butyloctyl)thiopropionate]; 3,6,9-trioxaundecane-1,11-bis[3-(6-butyloctyl)thio-2-methylpropionate]; 3-oxapentane-1,5-bis[3-(6-butyloctyl) thiopropionate]; phenyl-[3-butyloctyl)thiopropionate]; phenyl-1,4-bis[3-(6-butyloctyl)thiopropionate]; naphthyl-1-[3-(6-butyloctyl)thiopropionate]; naphthyl-2-[3-(6-butyloctyl)2-methyl thiopropionate]; naphthyl-1,4-bis[3-(6-butyloctyl)thiopropionate]; phenyl-[3-(6-butyloctyl)thio-2-methylpropionate]; benzyl-[3-(6-butyloctyl) thiopropionate]; benzyl-[3-(6-butyloctyl)thio-2-methylpropionate]; p-xylyl-alpha, alpha'-bis[3-(6-butyloctyl)-2-methylpropionate]; o-xylyl-alpha, alpha'-bis [3-(6 -butyloctyl)thiopropionate]; ethane-1,2-bis[3-(6-butyloctyl)thiopropionate]; butane-1,4-bis[3-(6-butyloctyl) thiopropionate]; pentane-1,5-bis[3-(6-butyloctyl)thio-2-methylpropionate]; propane-1,2-bis[3-(6-butyloctyl) thiopropionate]; octane-1,8-bis[3-(6-butyloctyl) thiopropionate]; 3,6,9-trioxaundecane-1,11-bis[3-(6-butyloctyl)thiopropionate]; 3,6,9-trioxaundecane-1,11-bis [3-(6-butyloctyl)thio-2-methyl-propionate]; 3-oxapentane-1,5-bis[3-(6-butyloctyl)thio-2-methylpropionate]; 3-thiapentane-1,5-bis[(6-butyloctyl)thio-2-methylpropionate]; 1,1,1-trimethanolpropane-tris[3-(6-butyloctyl)thiopropionate]; 1,1,1-trimethanolpropane-bis[3-(6-butyloctyl)thiopropionate]; pentaerythritol-tetrakis[3-(6-butyloctyl)thiopropionate]; and pentaerythritol-tetrakis[3-(2-butyloctyl)thio-2-methyl-propionate].

The above esters can be prepared by reacting a mercaptan with an ester of acrylic or methacrylic acid. Representative mercaptans include 2-ethyldecyl mercaptan, 2-butyloctyl mercaptan, 3-butyloctyl mercaptan, 4-butyloctyl mercaptan, 5-butyloctyl mercaptan, 6-butyloctyl mercaptan, 2-dodecyl mercaptan and mixtures thereof.

The above esters can be prepared by reacting the mercaptan with an ester of acrylic or methacrylic acid in the presence of a basic catalyst such as potassium hydroxide, benzyltrimethylammonium hydroxide and tetramethylammonium hydroxide and other suitable catalysts known in the art. The alkyl thiopropionate ester is then transesterified with a high molecular weight glycol. The method of U.S. Pat. No. 5,093,517 may be used to prepare the esters of the present invention. U.S. Pat. No. 5,093,517 is incorporated by reference in its entirety.

The representative high molecular weight glycols are of the formula

wherein $R^1$ and n is defined above.

The esters of the present invention may be used in combination with amine and/or phenolic antioxidants.

Typical of the phenolic antioxidants with stabilizing properties that are improved by the synergists of the present invention are phenolic compounds having the general formula:

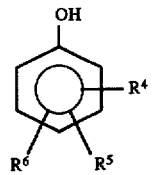

wherein $R^4$ is a tertiary alkyl radical having 4 to 8 carbon atoms, a cycloalkyl radical having 5 to 12 carbon atoms, or an aralkyl radical having 7 to 12 carbon atoms, and wherein $R^5$ and $R^6$ are alkyl radicals having 1 to 12 carbon atoms, cycloalkyl radicals having 5 to 12 carbon atoms, or aralkyl radicals having 7 to 12 carbon atoms; or polyphenolics of the formula:

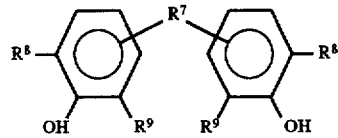

wherein $R^7$ is divalent radical having 1 to 4 carbon atoms, the group —O—, or the group —S—, and wherein $R^8$ and $R^9$ are alkyl radicals having 1 to 12 carbon atoms, cycloalkyl radicals having 5 to 12 carbon atoms, or aralkyl radicals having 7 to 12 carbon atoms. Preferably at least one of $R^8$ and $R^9$ is a tertiary alkyl radical having 4 to 8 carbon atoms and is in a position ortho to hydroxy group.

Other antioxidants such as:

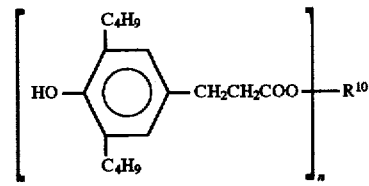

are useful with the synergists of this invention wherein n is an integer from 1 to 4 and $R^{10}$ is an alkyl radical having 8 to 20 carbon atoms, an alkylene radical having 2 to 6 carbon atoms, a thiodialkylene radical wherein each alkylene radical has 2 to 6 carbon atoms, a trivalent radical derived from a straight or branched chain hydrocarbon having 3 to 8 carbon atoms, or a tetravalent radical derived from a straight or branched chain hydrocarbon having 1 to 8 carbon atoms.

Representative of the phenolic antioxidants applicable in the present invention include: 2,6-di-tert-butyl-4-methylphenol; 2,4,6-tri-tert-butylphenol; 2,2'-methylene-bis-(4-methyl-6-tert-butylphenol); 2,2'-thio-bis-(4-methyl-6-tert-butylphenol); 4,4'-thio-bis-(3-methyl-6-tert-butylphenol); 4,4'-butylidene-bis-(6-tert-butyl-3-methylphenol); styrenated phenol; butylated octylated phenol; butylated-α-methylstyrenated phenol; styrenated butylated m and/or p-cresol; 4,4'-methylene-bis-(2,6-di-tert-butylphenol); 2,2'-methylene-bis-[4-methyl-6-(1-methylcyclohexyl)phenol], 2,5-diamylhydroquinone; 2,6-di-tert-butyl-4-butylthiophenol; butylated reaction product of p-cresol and dicyclopentadiene; tetrakis[methylene-3-(3, 5-di-tert-butyl-4-hydroxyphenyl)propionate]methane; 1,3, 5-trimethyl-2,4,6-tris-(3,5-di-tert-butyl-4-hydroxybenzyl) benzene; thiodiethylene-bis-[3-(3,5-di-tert-butyl-4-hydroxyphenyl)propionate]; octadecyl 3-(3,5-di-tert-butyl-4-hydroxyphenyl) propionate; and 2,6-bis-(1-phenylethyl)-4-(1-phenylethylthio)phenol.

Typical of the amine antioxidants with stabilizing properties that are improved by the addition of synergists of the present invention are the naphthylamines, diphenylamine derivatives, quinolines, paraphenylenediamines and the blended amines. A diphenylamine derivative especially useful is the alkylated diphenylamine known as Wingstay™ 29 (The Goodyear Tire & Rubber Company). The quinoline antidegradants are of two types-the polymerized and the non-polymerized dihydroquinolines and the substituted dihydroquinolines. Numerous paraphenylenediamines have been produced and used as antiozonants and benefit from the use of the synergists of this invention. Representative examples are Wingstay™ 200 and 100 (products of The Goodyear Tire & Rubber Company), Flexzone™ 3C and 6H (products of Uniroyal, Inc).

Another class of antidegradant that is useful with the synergists of the instant invention are the polymer bound antidegradants. Numerous investigators have studied the stabilizing properties of polymers that have as one of their segmeric units, an antioxidant functionality. A more complete discussion of suitable polymeric antidegradants useful with the synergists of the present invention can be found in U.S. Pat. Nos. 3,984,372, 3,962,187, 3,953,402, 3,953,411, 4,097,464, 4,152,319 and 3,658,769.

The synergists of the present invention have as one of their characteristic properties, the ability to vastly improve the effect of numerous compounds which are presently used as antioxidants or antiozonants for organic materials. While the synergists of the present invention may not be considered as stabilizers in their own right, their properties are such that they would be more conventionally classified as "synergists", in that, when combined with known stabilizers, they exhibit the ability to increase stabilization to a degree far exceeding that which would be expected from the additive properties of the individual components. The compounds of the present invention may also be used to more easily solubilize high melting rubber chemicals and prepare emulsions with higher solids content with greater stabilities and lower viscosities.

The compounds of the instant invention may be used with stabilizers or antidegradants (i.e. antioxidants, U.V. absorbers and antiozonants) at a weight ratio of from 1:50 to 50:1 synergist to antidegradant. However, the maximum effectiveness of the antidegradants is usually achieved when a compound of the instant invention is used with an antidegradant at ratios varying from 1:10 to 10:1. The optimum ratio of a given combination varies depending on the organic material to be stabilized, the antidegradants used and the environment to which the organic material is to be exposed. It should be appreciated that one or more synergists of the instant invention may be combined with one or more antidegradants of different types, (i.e. phenolics and amines).

The synergists or the stabilization system according to the present invention (synergist plus antidegradant) can be added to said organic materials in known ways. For instance, it can be combined with the oxidizable organic material either after dilution with a solvent, an emulsion while in latex form or directly as is, depending on the oxidizable material to be stabilized.

The synergists of this invention also may have a plasticizing effect on the polymers that they are added to. Those skilled in the art will readily appreciate the benefits of a plasticizing synergist.

Polymers, oils, resins and waxes subject to oxidation (oxidizable materials) that can be conveniently protected by the stabilization system described herein include substituted and unsubstituted, saturated and unsaturated, natural and synthetic polymers, oils, fuels and waxes. The oxidizable natural polymers include natural rubber in its various forms, e.g., pale crepe and smoked sheet, and balata and gutta percha. The oxidizable synthetic polymers are prepared from a single monomer (homopolymer) or a mixture of two or more copolymerizable monomers (copolymer) wherein the monomers are combined in a random distribution or block form. The monomers may be substituted or unsubstituted and may possess one or more double bonds, for example, diene monomers, both conjugated and nonconjugated, and monoolefins including cyclic and acyclic monoolefins, especially vinyl and vinylidene monomers. Examples of conjugated dienes are 1,3-butadiene, isoprene, chloroprene, 2-ethyl-1,3-butadiene, 2,3-dimethyl-1,3-butadiene and piperylene. Examples of nonconjugated dienes are 1,4-pentadiene, 1,4-hexadiene, 1,5-hexadiene, dicyclopentadiene, 1,5-cyclooctadiene and ethylidene norbornene. Examples of acyclic monoolefins are ethylene, propylene, 1-butene, isobutylene, 1-pentene and 1-hexene. Examples of cyclic monoolefins are cyclopentene, cyclohexene, cyclooctene and 4-methyl-cyclooctene. Examples of vinyl monomers are styrene, acrytonitrile, acrylic acid, ethylacrylate, vinyl chloride, butylacrylate, methyl vinyl ether, vinyl acetate and vinyl pyridine. Examples of vinylidene monomers are α-methylstyrene, methacrylic acid, methyl methacrylate, itaconic acid, ethyl methacrylate, glycidyl methacrylate and vinylidene chloride. Representative examples of the synthetic polymers are polychloroprene; carboxylated acrylonitrile-butadiene copolymers, carboxylated styrene-butadiene copolymers, acrylonitrile butadiene copolymers, styrene-butadiene copolymers, isoprene-butadiene copolymers, polybutadiene, synthetic polyisoprene, styrene-isoprene-butadiene terpolymers, styrene-isoprene copolymers, polyurethanes containing carbon to carbon double bonds; and polymers and copolymers of monoolefins containing little or no unsaturation, such as polyethylene, polypropylene, ethylene propylene copolymers and terpolymers of ethylene, propylene and a nonconjugated diene such as dicyclopentadiene, 1,4-hexadiene, ethylidene norbornene and methylene norbornene and polyester.

It has been found that addition of the synergist and the antidegradant (stabilization system) to organic materials in the range from 0.01 to 10.0 parts by weight per hundred parts by weight of organic material will effectively protect the organic material from deterioration. As described, the stabilization system according to the present invention comprises the novel compounds in combination with a known antidegradant. The stabilization system of the present invention demonstrates activity superior to that of most conventional systems prepared by combining two or more commercial stabilizers.

EXAMPLE

The following example was conducted to demonstrate the preparation of the esters of the present invention. A mixture of secondary mercaptan was used which was obtained from Elf Atochem and identified as containing 2-dodecyl mercaptan and isomers of butyloctyl mercaptan. Into a 1-liter flask equipped with a stirrer, drop funnel, thermometer and condenser was weighed 202 g of the mixture of mercaptans and 15 drops of benzyltrimethylammonium hydroxide commercially identified as Triton™ B.

To the contents of the flask was added dropwise 98 grams of methyl acrylate over a 20 minute period below 70° C. After 90 minutes of reaction, gas chromatography indicated 99.7 percent of the desired first-step reaction products. The product was stripped at 78° C. under vacuum to remove the excess methyl acrylate. The first-stage reaction product weighed 288 g.

Into a 500 ml reactor containing a thermometer, stirrer and volatile releasing line leading through a dry ice trap to an aspirator vacuum was added 250 g of the above first-stage reaction product. To it was added 84.2 g tetraethylene glycol and 1.70 g dibutyltin oxide. The flask contents were reacted under vacuum (≈15 mm Hg) while checking for formation of the desired end-product every 15 minutes for 1.5 hours. Gel permeation chromatography (GPC) was used to analyze the end-product. Data are shown in Table I below.

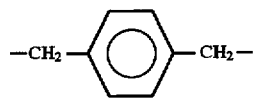

polyalkyl glycol ether radicals having the following structure

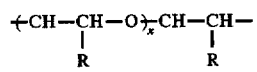

wherein x is an integer from 1 to 7, a thioether radical having the following structure

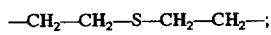

$R^2$ is an alkylene radical selected from the group consisting of 6 and 9 carbon atoms; $R^3$ is an alkyl radical selected from the group consisting of 1 and 4 carbon atoms; with the proviso that the total sum of the number of carbon atoms for $R^2$ and $R^3$ equal 10.

2. The compound of claim 1 wherein x is 3.

3. The compound of claim 1 wherein x is 4.

TABLE I

RESULTS OF LOW MOLECULAR WEIGHT GPC ANALYSIS

| Polystyrene Standards | Columns: Phenogel- 1-50A, 2-100A, |
| Solvent: Tetrahydrofuran | 1-500A, 1-5000A |
| Inj Size: 100 ul | Sample Conc: 0.25% |
| Exclusion Limit: 40,000 MW | Detectors: RI |

| Component | RT, min | MW (at peak max) | Area % |
|---|---|---|---|
| Unknown | 31.6 | 1510 | 0.2 |
| Bis Product[1] | 33.5 | 830 | 73.6 |
| Mono Product[2] | 35.4 | 510 | 15.4 |
| Unknown | 36.8 | 370 | 1.0 |
| 1st Stage Product | 38.0 | 290 | 9.1 |
| Tetraethylene glycol | 40.3 | 200 | 0.7 |

1. 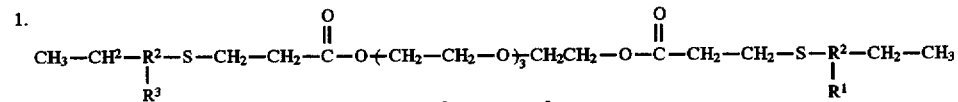
where when $R^2$ is $C_9H_{18}$, $R^3$ is $CH_3$ and where when $R^2$ is $C_6H_{12}$, $R^3$ in $C_4H_9$.

2. 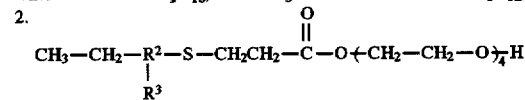
where when $R^2$ is $C_9H_{18}$, $R^3$ is $CH_3$ and where when $R^2$ is $C_6H_{12}$, $R^3$ in $C_4H_9$.

What is claimed is:

1. A compound of the formula

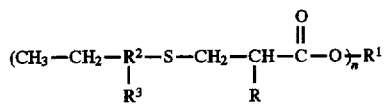

wherein n is 2, R is selected from the group consisting of hydrogen and methyl; $R^1$ is selected from the group consisting of alkylene radicals having 2 to 18 carbon atoms, cycloalkylene radicals having 5 to 12 carbon atoms, arylene radicals having 6 to 12 carbon atoms, 4. The compound of claim 1 wherein R is hydrogen.

5. A stable organic composition which comprises (a) an oxidizable organic material selected form the group consisting of polymers, oils, resins and waxes, (b) a phenolic and/or amine antidegradant and (c) the compound of claim 1.

6. The stable organic composition of claim 5 wherein said polymer is selected from the group consisting of natural rubber, carboxylated acrylonitrile-butadiene copolymers, carboxylated styrene-butadiene copolymers, acrylonitrile-butadiene copolymers, styrene-butadiene copolymers, isoprene-butadiene copolymers, polybutadiene, synthetic polyisoprene, styrene-isoprene-butadiene terpolymers, styrene-isoprene copolymers, polyurethanes, polyethylene, polypropylene, ethylene-propylene copolymers, terpolymers of ethylene-propylene and a nonconjugated diene and polyester.

7. The stable organic composition of claim 5 wherein said phenolic antidegradant is of the formula:

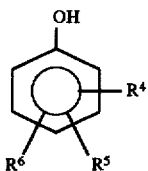

wherein $R^4$ is a tertiary alkyl radical having 4 to 8 carbon atoms, a cycloalkyl radical having 5 to 12 carbon atoms, or an aralkyl radical having 7 to 12 carbon atoms, and wherein $R^5$ and $R^6$ are alkyl radicals having 1 to 12 carbon atoms, cycloalkyl radicals having 5 to 12 carbon atoms, or aralkyl radicals having 7 to 12 carbon atoms.

8. The stable organic composition of claim 5 wherein said phenolic antidegradant is of the formula

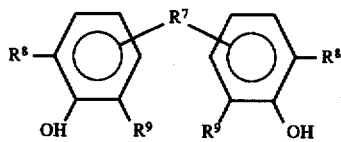

wherein $R^7$ is divalent radical having 1 to 4 carbon atoms, the group —O—, or the group —S—, and wherein $R^8$ and $R^9$ are alkyl radicals having 1 to 12 carbon atoms, cycloalkyl radicals having 5 to 12 carbon atoms, or aralkyl radicals having 7 to 12 carbon atoms.

9. The stable organic composition of claim 5 wherein said phenolic antidegradant is of the formula:

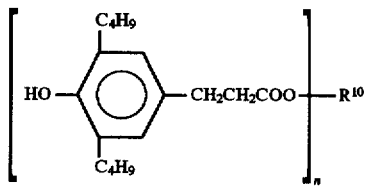

wherein n is an integer from 1 to 4 and $R^{10}$ is an alkyl radical having 8 to 20 carbon atoms, an alkylene radical having 2 to 6 carbon atoms, a thiodialkylene radical wherein each alkylene radical has 2 to 6 carbon atoms, a trivalent radical derived from a straight or branched chain hydrocarbon having 3 to 8 carbon atoms, or a tetravalent radical derived from a straight or branched chain hydrocarbon having 1 to 8 carbon atoms.

10. The stable organic composition of claim 5 wherein said amine antidegradant is selected from the group consisting of naphthylamines, diphenylamine derivatives, quinolines and paraphenylenediamines.

11. The stable organic composition of claim 5 wherein the weight ratio of the compound of claim 1 to antidegradant ranges from 1:50 to 50:1.

12. The stable organic composition of claim 5 wherein from 0.01 to 10.0 parts per weight per hundred parts by weight of organic material is present.

* * * * *